US00PP22399P2

(12) United States Plant Patent
Hooijman

(10) Patent No.: US PP22,399 P2
(45) Date of Patent: Dec. 27, 2011

(54) ROSE PLANT NAMED 'ESM TECNO'

(50) Latin Name: *Rosa hybrida*
Varietal Denomination: Esm Tecno

(75) Inventor: Aloysius A. J. Hooijman, Aalsmeer (NL)

(73) Assignee: Esmeralda Breeding B. V., Aalsmeer (NL)

( * ) Notice: Subject to any disclaimer, the term of this patent is extended or adjusted under 35 U.S.C. 154(b) by 0 days.

(21) Appl. No.: 12/927,782

(22) Filed: Nov. 22, 2010

(51) Int. Cl.
*A01H 5/00* (2006.01)

(52) U.S. Cl. ..... Plt./102

(58) Field of Classification Search ..... Plt./102
See application file for complete search history.

*Primary Examiner* — Kent L Bell
(74) *Attorney, Agent, or Firm* — C. A. Whealy

(57) ABSTRACT

A new and distinct cultivar of Rose plant named 'Esm Tecno', characterized by its strong and upright flowering stems; moderately vigorous growth habit; early flowering habit; large creamy white and yellow-colored flowers with light peach tonality; and good postproduction longevity.

1 Drawing Sheet

Botanical designation: *Rosa hybrida.*
Cultivar denomination: 'ESM TECNO'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'Esm Tecno'.

The new Rose plant is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new Rose plant originated from a cross-pollination made by the Inventor in February, 2002 of a proprietary Rose selection identified as code name Line 34, not patented, as the female, or seed, parent with a proprietary Rose selection identified as code name Line 10, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in March, 2003.

Asexual reproduction of the new Rose plant by cuttings at El Quinche, Pichincha, Ecuador since November, 2004, has shown that the unique features of this new Rose plant are stable and reproduced true to type in successive generations of asexual reproduction.

SUMMARY OF THE INVENTION

Plants of the new Rose have not been observed under all possible environmental conditions. The phenotype may vary somewhat with variations in environment such as temperature and light intensity, without, however, any variance in genotype.

The following traits have been repeatedly observed and are determined to be the unique characteristics of 'Esm Tecno'. These characteristics in combination distinguish 'Esm Tecno' as a new and distinct Rose plant:

1. Strong and upright flowering stems.
2. Moderately vigorous growth habit.
3. Early flowering habit.
4. Large creamy white and yellow-colored flowers with light peach tonality.
5. Good postproduction longevity.

Plants of the new Rose differ from plants of the female parent selection in the following characteristics:

1. Plants of the new Rose are taller than plants of female parent selection.
2. Plants of the new Rose have larger flowers than plants of the female parent selection.
3. Plants of the new Rose and the female parent selection differ in flower color as plants of the female parent selection have red-colored flowers.

Plants of the new Rose differ from plants of the male parent selection in the following characteristics:

1. Plants of the new Rose are taller than plants of the male parent selection.
2. Plants of the new Rose and the male parent selection differ in flower color as plants of the male parent selection have yellow-colored flowers.

Plants of the new Rose can be compared to plants of Rose 'Fenice', not patented. In side-by-side comparisons conducted in El Quinche, Pichincha, Ecuador, plants of the new Rose differed from plants of 'Fenice' in the following characteristics:

1. Plants of the new Rose were not as vigorous as plants of 'Fenice'.
2. Plants of the new Rose flowered earlier than plants of 'Fenice'.
3. Flowers of plants of the new Rose were more fragrant than flowers of plants of 'Fenice'.
4. Plants of the new Rose and 'Fenice' differed in flower color as plants of 'Fenice' had creamy pink-colored flowers.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the left of the sheet comprises a side perspective view of a typical flowering stem of 'Esm Tecno'.

The photograph at the upper right of the sheet is a close-up view of a typical flower of 'Esm Tecno'.

The photograph at the bottom left of the sheet is a close-up view of typical flowers of 'Esm Tecno'.

The photographs at the center right of the sheet are close-up views of the upper and lower surfaces of typical leaves of 'Esm Tecno'.

The photograph at the lower right is a close-up view of an opening flower of 'Esm Tecno'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown in 10-cm containers in a polyethylene-covered greenhouse in El Quinche, Pichincha, Ecuador and under typical hydroponic Rose production practices. Plants were pinched about 13 to 14 weeks after planting. Plants were four years old when the photographs and description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm Tecno'.

Parentage:

- *Female, or seed, parent.*—Proprietary seedling selection of *Rosa hybrida* identified as code name Line 34, not patented.
- *Male, or pollen, parent.*—Proprietary seedling selection of *Rosa hybrida* identified as code name Line 10, not patented.

Propagation:

- *Type.*—By cuttings.
- *Time to initiate roots.*—About seven to ten days at 26° C. to 30° C.
- *Time to produce a rooted young plant.*—About four to five weeks at 22° C. to 26° C.
- *Root description.*—Fibrous, fine; close to N199B in color.
- *Rooting habit.*—Freely branching; medium density.

Plant description:

- *Plant form.*—Upright plant habit; strong and upright flowering stems.
- *Growth habit.*—Moderately vigorous; freely basal branching habit; dense and bushy growth habit; about 13.2 flowering stems develop per year.
- *Plant height.*—About 75 cm.
- *Plant width (spread).*—About 56 cm.
- *Lateral branches (peduncles).*—Length: About 75 cm. Diameter: About 5.9 mm. Internode length: About 5.6 cm. Texture: Smooth, glabrous. Color: Close to 146A. Thorns: Density: Medium density. Shape: Triangular with sharp acuminate apices; slightly incurved. Height: About 6.4 mm. Length, at base: About 6.8 mm. Color, immature: Close to 178B. Color, mature: Close to 166B and 153B.

Foliage description:

- *Arrangement.*—Alternate; compound with typically seven leaflets per leaf.
- *Leaf length.*—About 18.9 cm.
- *Leaf width.*—About 11.5 cm.
- *Terminal leaflet length.*—About 6.2 cm.
- *Terminal leaflet width.*—About 3.9 cm.
- *Lateral leaflet length.*—About 5.5 cm.
- *Lateral leaflet width.*—About 3.6 cm.
- *Leaflet shape.*—Oval.
- *Leaflet apex.*—Acute.
- *Leaflet base.*—Attenuate.
- *Leaflet margin.*—Serrate.
- *Leaflet texture, upper and lower surfaces.*—Smooth, glabrous.
- *Leaflet venation pattern.*—Pinnate.
- *Leaflet color.*—Developing leaflets, upper surface: Close to 137A; towards the margins, close to 200A. Developing leaflets, lower surface: Close to 147B. Fully expanded leaflets, upper surface: Close to 139A; venation, close to N144A. Fully expanded leaflets, lower surface: Close to 147B; venation, close to 146D.
- *Petioles, leaves.*—Length: About 2 cm. Diameter: About 1.9 mm. Texture, upper and lower surfaces: Smooth, glabrous. Color, upper surface: Close to 144A and 145B. Color, lower surface: Close to 146B.
- *Petioles, leaflets.*—Length: About 2.5 cm. Diameter: About 1.1 mm. Texture, upper and lower surfaces: Smooth, glabrous. Color, upper surface: Close to 144A. Color, lower surface: Close to 146A.
- *Stipules.*—Arrangement and appearance: Two, adnate to the petiole, leafy. Length: About 2.4 cm. Width: About 3 mm. Shape: Roughly deltoid. Apex: Acuminate. Base: Truncate. Margin: Serrate, irregular. Texture, upper and lower surfaces: Smooth, glabrous; pubescent along the margins. Venation pattern: Pinnate. Color, upper surface: Close to 147A. Color, lower surface: Close to 146A.

Flower description:

- *Flower type and habit.*—Symmetrical rosette flowers; typically grown as a single stem.
- *Flowering season.*—Year-round under greenhouse conditions; early flowering habit, plants begin flowering about 63 days after pinching; in the garden, optimal flowering from spring through autumn; flowering intermittent.
- *Flower diameter.*—About 12 cm.
- *Flower depth (height).*—About 5.4 cm.
- *Flower longevity on plant.*—About 22 days; flowers persistent.
- *Flower longevity as a cut flower.*—About ten days.
- *Fragrance.*—Moderately fragrant, pleasant.
- *Flower buds.*—Shape: Cupped. Length: About 5.2 cm. Diameter: About 3 cm. Color: Close to 144A.
- *Petals.*—Quantity: About 28 per flower; petals imbricate. Length: About 5.5 cm. Width: About 5.8 cm. Shape: Nearly round; transversely ovate. Apex: Blunt to short acute. Base: Obtuse. Margin: Entire. Texture, upper and lower surfaces: Smooth, glabrous; papery to coriaceous. Color: When opening, upper surface: Close to 164D; towards the base, close to 1A. When opening, lower surface: Close to 158A; towards the base, close to 151D. Fully opened, upper surface: Close to 158A; towards the base, close to 7B; tonality, light peach. Fully opened, lower surface: Close to 159B; towards the base, close to 7B; inner petals, close to 159A.

*Sepals.*—Quantity per flower: Typically five. Length: About 4.4 cm. Width: About 1.3 cm. Shape: Roughly deltoid. Apex: Tapered. Base: Truncate. Margin: Entire; ciliate. Texture, upper and lower surfaces: Pubescent; coriaceous. Color: When opening, upper surface: Close to 143C. When opening, lower surface: Close to 144A. Fully opened, upper surface: Close to 137C and 146D. Fully opened, lower surface: Close to 144A.

*Reproductive organs.*—Stamens: Quantity: About 132 per flower. Anther length: About 3.6 mm. Anther shape: Reniform. Anther color: Close to 162A; towards the margins, close to N163D. Filament color: Close to 163B and 2C. Pollen amount: Abundant. Pollen color: Close to 167C. Pistils: Quantity: About 100 per flower. Pistil length: About 1.7 cm. Stigma shape: Broadly reniform. Stigma color: Close to 160A. Style length: About 1 cm. Style color: Close to 145C. Receptacle height: About 1.3 cm. Receptacle diameter: About 1.1 cm. Receptacle shape: Cup-shaped. Receptacle texture: Smooth, glabrous. Receptacle color: Close to 144A. Fruits: Length: About 2.5 cm. Diameter: About 1.7 cm. Texture: Smooth. Color: Close to 146D becoming closer to 167D with development. Seeds: Quantity per fruit: About ten. Length: About 7 mm. Diameter: About 5 mm. Texture: Smooth. Color: Close to 153D.

Pathogen/pest resistance: Plants of the new Rose have been observed to be resistant to Botrytis. Plants of the new Rose have not been observed to be resistant to pests and other pathogens common to Roses.

Temperature tolerance: Plants of the new Rose have been observed to tolerate temperatures ranging from 0° C. to 35° C.

It is claimed:

1. A new and distinct Rose plant named 'Esm Tecno' as illustrated and described.

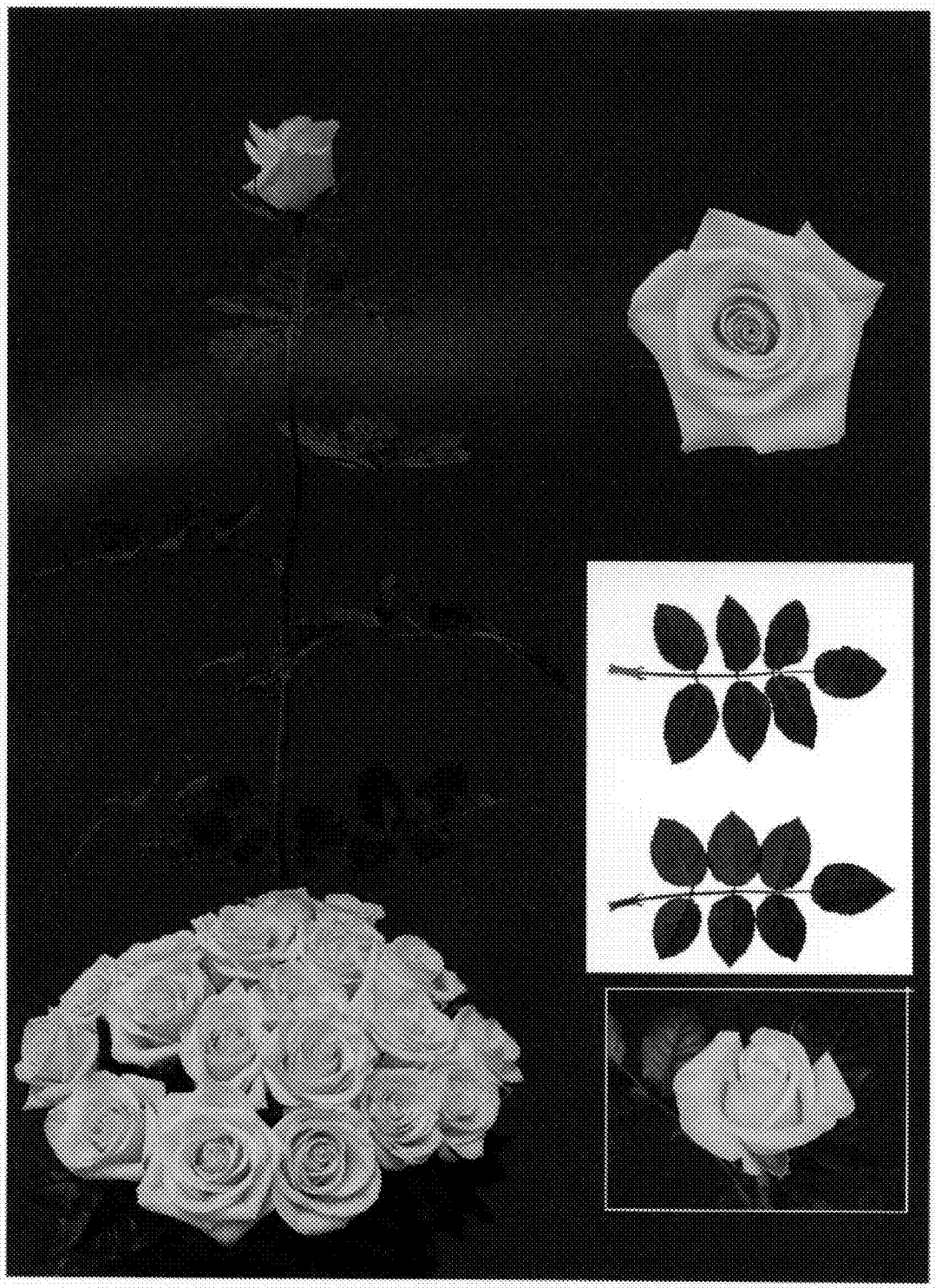

* * * * *